United States Patent [19]

Freyria et al.

[11] Patent Number: 4,585,794
[45] Date of Patent: Apr. 29, 1986

[54] METHOD FOR TREATING RENAL INSUFFICIENCY

[75] Inventors: Jean Freyria, Vaucresson; Brigitte Lantz, Paris, both of France

[73] Assignee: ADIR, S.A.R.L., Neuilly-sur-Seine, France

[21] Appl. No.: 694,710

[22] Filed: Jan. 25, 1985

Related U.S. Application Data

[63] Continuation-in-part of Ser. No. 516,936, Jul. 25, 1983, abandoned.

[30] Foreign Application Priority Data

Jul. 29, 1982 [FR] France .................................. 82 13232

[51] Int. Cl.$^4$ ............................................. A61K 31/24
[52] U.S. Cl. ................................................... 514/434
[58] Field of Search ........................................ 514/434

[56] References Cited

U.S. PATENT DOCUMENTS 3,960,891 6/1976 Malen et al. ........................... 549/23
4,032,648 6/1977 Malen et al. .......................... 424/275

FOREIGN PATENT DOCUMENTS 2498930 8/1982 France .................................. 424/275

OTHER PUBLICATIONS

Page 948 and Cover Sheet of "Cardiac and Vascular Diseases" by Conn and Horwitz, vol. II by Lea and Febiger, Philadelphia (1971).
Drugs 23: 195–206 (1982); Review Article by Robert Wilkinson; Title: "Beta-Blockers and Renal Function".
Ljungman S., et al., Blood Pressure and Renal Function, Acta Med. Scand. 208, 17–25, (1980).
Epstein M., et al., Beta-Blockers and the Kidney, Min. Electrolyte Metab. 8, 237–254 (1982).
Berglung G., et al., Pharmacokinetics of Sotalol after Chronic Administration to Patients with Renal Insufficiency, Eur. J. Clin. Pharmacol, 18, 321–326, (1980).
Bianchi G., et al., A Renal Abnormality as a possible cause of "Essential" Hypertension, Lancet I, 173–177, (1979).
Bianchi, G., et al., Renal Dysfunction as a possible cause of Essential Hypertension in Predisposed Subjects, Kidney Int. 23, 870–875, (1983).
Hollenberg N. K., et al., "No Man's Land" of the Renal Vasculature, An Arteriographic and Hemodynamic Assessment in the Interlobar and Arcuate Arteries in Essential and Accelerated Hypertension, Am. J. Med. 47, 845–852, (1969).
Danesh B. J. Z., et al., Nadolol and Renal Haemodynamics, Proc. R. Soc. Med. 37, 87–95 (1981).
Warren D., et al., Deterioration in Renal Function after Beta-Blockade in Patients with Chronic Renal Failure and Hypertension, Br. Med., J. 2, 193–194 (1974).
Swainson C. P., et al., Effect of Beta Blockade in Chronic Renal Failure, Br. Med. J. 459, (1976).
Leary W. P., et al., Effect of Beta-Blocking Agents on Renal Function, S. Afr. Med. J. 56, 745 (1979).
O'Connor D. T., et al., Preserved Renal Perfusion during Treatment of Essential Hypertension with the Beta-Blocker Nadolol, J. Clin. Pharmacol. 22, 187–195, (1982).
Britton K. E., et al., Nadolol and Renal Haemodynamics, Proc. R. Soc. Med. 37, 77–85, (1981).
Pedersen E. B.: Glomerular Filtration Rate and Renal Plasma Flow in Patients with Essential Hypertension before and after Treatment with Alprenolol, Acta Med. Scand. 198, 365–371, (1975).
Wilcox C. S., et al., Renal Function, Body Fluid Volumes, Renin, Aldosterone, and Noradrenaline during Treatment of Hypertension with Pindolol, J. Cardiovasc. Pharmacol. 3, 598–611, (1981).
Zech P. Y., et al., Response to Atenolol in Arterial Hypertension in Relation to Renal Function, Pharmacokinetics and Renin Activity, Postgrad. Med. J. 53, suppl. 3, 134–141, (1977).
Wilkinson R., et al., A Study of the Effects of Atenolol and Propranolol on Renal Function in Patients with Essential Hypertension, Br. J. Clin. Pharmaco. 10, 51–59, (1980).
O'Connor D. T., et al., Urinary Kallikrein Activity, Renal Hemodynamics, and Electrolyte Handling During Chronic Beta Blockade with Propanolol in Hypertension, Hypertension 4, 742–749, (1982).
Pedersen, E. B.: Effect of Sodium Loading and Exercise on Renal Haemodynamics and Urinary Sodium Excretion in Young Patients with Essential Hypertension Before and During Propranolol Treatment, Acta Med. Scand. 201, 365–373, (1977).
Warren, S. E., et al., Renal Hemodynamic Changes During Long-Term Antihypertensive Therapy, Clin. Pharmacol. Ther. 29, 310–317 (1981).
O'Connor, D. T., et al., Renal Perfusion Changes During Treatment of Essential Hypertension: Prazosin versus Propranolol, J. cardiovas. Pharmacol., suppl. 1, 38–42, (1979).
Bauer, J. H., et al., The Long-Term Effect of Propranolol Therapy on Renal Function, Am. J. Med. 66, 405–410, (1979).

*Primary Examiner*—Stanley J. Friedman
*Attorney, Agent, or Firm*—Gordon W. Hueschen

[57] ABSTRACT

The invention relates to a method for preventing or treating renal insufficiency with a composition containing as active ingredient 8-(3-tert.-butylamino-2-hydroxypropoxy)thiachroman, or one of the addition salts thereof with a mineral or organic acid, in combination or in admixture with an inert pharmaceutically acceptable, non-toxic excipient or carrier.

4 Claims, No Drawings

METHOD FOR TREATING RENAL INSUFFICIENCY

This application is a continuation in part of our prior filed co-pending application, Ser. No. 516,936 filed July 25, 1983, now abandoned.

The invention relates to a method for preventing or treating renal insufficiency by increasing renal glomerular filtration rate and renal plasma flow in hypertensive patients in need thereof with 8-(3-tert.-butylamino-2 hydroxypropoxy)-thiachroman.

The invention comprises the use of a pharmaceutical composition having a renal vasodilatory property and containing as active ingredient 8-(3-tert.-butylamino-2-hydroxypropoxy)-thiachroman, or one of the addition salts thereof with a mineral or organic acid, in combination or in admixture with an inert, pharmaceutically acceptable, non toxic excipient or carrier.

The compound used according to the invention has been described in Example 2 of U.S. Pat. Nos. 3,960,891 and 4,032,648 (MALEN et al.), in which it is described as having beta-blocking properties.

The renal vasodilatory property is, however, completely separate from the beta-blocking properties previously described in the above-mentioned patents and in the publication of Laubie et al., C.R. Acad. Sci. (1971), 273 (D), 1243, and is not found in the know beta-blockers, such as, for example, alprenolol, propranolol, practolol, nadolol, etc.

8-(3-tert.-butylamino-2-hydroxypropoxy)-thiachroman, referred to hereinafter as "THPT", contains one asymmetric carbon atom in the side chain. It may be resolved to give the laevorotatory and dextrorotatory isomers.

The pharmaceutical composition, having the properties according to the invention, contains from 2 to 10 mg of one or the other of the optical isomers of 8-(3-tert.-butylamino-2- hydroxypropoxy)-thiachroman, or one of the addition salts thereof with a mineral or organic acid, in admixture with an inert, pharmaceutically acceptable, non-toxic excipient.

As addition salts with a mineral acid there may be mentioned the hydrochloride, the hydrobromide, the phosphate, the hydriodide or the perchlorate; as addition salt with an organic acid there may be mentioned the formate, the acetate, the butyrate, the lactate, the tartrate, the pyruvate, the maleate or fumarate, the benzoate, the nicotinate, etc.

The invention is based on the fact that the composition according to the invention has been found to increase the glomerular filtration rate and the renal plasma flow, in contrast to the known beta-blockers, especially propranolol, pindolol or oxprenolol, which considerably decrease these activities (of the order of 30 %), making their use dangerous, or completely impossible, in the treatment of hypertension associated with renal insufficiency.

Renal hemodynamic alteration induces a decrease of the sodium ($Na^+$) excretion. The resultant sodium retention tends to limit the antihypertensive effect of the known beta-blockers. Sodium retention is a well known adverse effect of these drugs.

The pharmacological tests and clinical trials carried out with the composition reveal the fact that THPT significantly increases the glomerular filtration rate, the renal plasma flow and the sodium excretion in normotensive dogs. Additionaly, clinical trials establish that the drug significantly increases the glomerular filtration rate and the renal plasma flow in patients suffering from hypertension and does not modify them significantly in normotensive patients with or without renal insufficiency.

As a result, the pharmaceutical composition according to the invention can be used for preventing and treating renal insufficiency, especially renal insufficiency induced or caused by hypertension, for it is well known that renal insufficiency very often accompanies hypertension and is a direct consequence thereof in the more or less long term.

Deterioration in renal function in patients with pre-existing renal failure is a well known side-effect during the treatment of hypertension by beta-adrenergic blocking drugs. Such effect has been reported by Dr. D. J. WARREN Am. Heart. J. (1976),91, No. 2, 265.

As we mentioned above, the acute and chronic oral administration of beta-blockers usually results in a reduction in effective renal plasma flow and glomerular filtration rate. The only exception is perhaps nadolol, the effects of which on the renal plasma flow depend on the mode of the administration, and the low sodium diet of the patients. Nadolol, however, does not increase glomerular filtration rate in any case.

The superiority of the invention is that it increases renal plasma flow in animals and in patients with or without a low sodium diet, and increases the glomerular filtration rate and sodium excretion.

Concerning the treatment of hypertension, subjects with normal renal function can be treated with all beta-blockers. Patients with renal impairment can be treated with nadolol or with the method of the invention. Patients with renal insufficiency can be treated only with the method of the invention.

The pharmaceutical composition according to the invention is preferably intended for administration by the oral route or, if desired, by the parental route. It may be presented especially in the form of plain or coated tablets, dragées, capsules, suspensions for drinking or also solutions for injection filled into ampoules, multi-dose bottles or syringes for self-injection.

The pharmaceutical composition according to the invention may also contain one or more excipients and diluents, binders, adhesion agents or disintegrating agents, lubricants or thickening agents. Amongst the latter there may be mentioned starches, potato starch, natural or chemically modified celluloses, methylcellulose, ethylcellulose, calcium carbonate and magnesium phosphate.

For solutions or suspensions, water or saline solutions are preferably used as carrier or solvent.

The daily dosage for adults is within the range of from 2 to 10 mg daily, preferably administered in one dose.

The following example illustrates the invention without limiting it in any way.

EXAMPLE 1

Tablet containing 5 mg of THPT, HCl

| | |
|---|---|
| (dl)-THPT,HCl | 5.000 mg |
| stearic acid | 0.490 mg |
| microcrystalline cellulose | 33.300 mg |
| sodium carboxymethyl starch | 3.000 mg |
| colloidal silica | 0.270 mg |
| lactose | 37.000 mg |
| glycerol | 0.044 mg |

-continued

| | |
|---|---|
| magnesium stearate | 0.490 mg |
| hydroxypropylmethylcellulose | 0.750 mg |
| sodium laurylsulphate | 0.035 mg |
| titanium oxide | 0.140 mg |
| dicalcium phosphate | 10.000 mg |
| polyoxyethylene glycol 6000 | 0.018 mg |
| white wax | q.s. |

A finished tablet has an average weight of 91 mg.

PHARMACOLOGICAL STUDIES IN DOGS

EXAMPLE 2

The renal haemodynamic effects of THPT were examined after intravenous administration of 0.05 mg/kg of the drug in normotensive conscious dogs. The glomerular filtration rate and the renal plasma flow were evaluated using the standard methods of clearance of inulin and para-aminohippuric acid (PAH).

In comparison to the control group, on the treated group were observed an increase in glomerular filtration rate (GFR) (inulin clearance) and a slight enhancement in effective renal plasma flow (PAH-clearance or $C_{PAH}$), without attendant decreases in plasma renin activity (PRA). An increase in urinary sodium excretion which may be related, in part, to a decrease in tubular reabsorption was also observed (Table 1).

mg/kg, n=8), these two doses being of equivalent beta-adrenolytic activity.

After administration of propranolol a significant decrease in plasma renin activity and effective renal plasma flow was observed without any change in glomerular filtration rate or sodium excretion. In contrast to propranolol, administration of THPT did not result in any modification of effective renal plasma flow. However, statistically a significant increase in glomerular filtration rate and sodium (Na+) excretion was observed. THPT also induced a significant decrease in plasma renin activity.

These results prove that propranolol and THPT have differing effects on renal hemodynamics in the conscious dog.

TABLE 2

| | To | 30 min. | 60 min. |
|---|---|---|---|
| $C_{PAH}$(ml/min) | | | |
| THPT | 196 ± 16 | 200 ± 16 | 191 ± 8 |
| Propranolol | 218 ± 14 | 188 ± 12 | 170 ± 12* |
| GFR (ml/min) | | | |
| THPT | 72 ± 5 | 81 ± 4 | 82 ± 4** |
| Propranolol | 66 ± 2 | 65 ± 2 | 67 ± 2 |
| PRA (ng.AgIml/h/) | | | |
| THPT | 2.2 ± 0.4 | 1.0 ± 0.1** | 0.7 ± 0.1** |
| Propranolol | 2.9 ± 1.2 | 1.9 ± 0.9* | 1.9 ± 0.8* |
| Na+Ur.(mEq/l) | | | |
| THPT | 70 ± 10 | 100 ± 7** | 105 ± 10** |
| Propranolol | 108 ± 18 | 95 ± 19 | 82 ± 20 | mean ± S.E.M.
Statistically significance: *p<0,05
**p<0,02

TABLE 1

| Time (min) | 0–20 | 20–40 | 40–60 | 60–80 | 80–100 | 100–120 |
|---|---|---|---|---|---|---|
| GFR (ml/min) | | | | | | |
| Control | 50.5 ± 5.0 | 54.0 ± 4.9 | 51.0 ± 4.9 | 53.6 ± 3.9 | 56.4 ± 5.8 | 59.8 ± 6.4 |
| THPT | 55.5 ± 3.3 | 57.3 ± 2.6 | 62.8 ± 8.1 | 67.7 ± 5.0 | 74.0 ± 4.9 | 62.0 ± 6.6 |
| | N.S. | N.S. | N.S. | p<0.02 | p = 0.057 | N.S. |
| $C_{PAH}$(ml/min) | | | | | | |
| Control | 193 ± 23 | 197 ± 24 | 194 ± 19 | 190 ± 17 | 200 ± 23 | 200 ± 22 |
| THPT | 206 ± 27 | 214 ± 25 | 222 ± 35 | 226 ± 24 | 241 ± 26 | 222 ± 27 |
| | N.S. | N.S. | N.S. | p = 0.087 | N.S. | N.S. |
| $U_{Na}V(\mu Eq/min)$ | | | | | | |
| Control | 63 ± 20 | 62 ± 17 | 60 ± 19 | 60 ± 18 | 46 ± 12 | 44 ± 12 |
| THPT | 48 ± 12 | 46 ± 10 | 50 ± 10 | 74 ± 19 | 107 ± 24 | 138 ± 38 |
| | N.S. | N.S. | N.S. | N.S. | p<0.01 | p<0.025 |
| Fractional sodium extraction | | | | | | |
| Control | 0.86 ± 0.24 | 0.87 ± 0.28 | 0.76 ± 0.23 | 0.78 ± 0.26 | 0.57 ± 0.13 | 0.52 ± 0.13 |
| THPT | 0.64 ± 0.18 | 0.56 ± 0.13 | 0.51 ± 0.14 | 0.87 ± 0.11 | 1.00 ± 0.27 | 1.62 ± 0.50 |
| | N.S. | N.S. | N.S. | N.S. | p<0.05 | p<0.05 |
| P.R.A. (ng AI/ml/hr) | | | | | | |
| Control | 0.83 ± 0.27 | 0.88 ± 0.33 | 0.80 ± 0.28 | 0.81 ± 0.30 | 0.83 ± 0.27 | 0.80 ± 0.28 |
| THPT | 0.94 ± 0.22 | 0.84 ± 0.19 | 0.84 ± 0.24 | 0.88 ± 0.34 | 1.01 ± 0.46 | 1.54 ± 1.00 |
| | N.S. | N.S. | N.S. | N.S. | N.S. | N.S. |

Mean ± S.E.M.
N.S.: Statistically not significant.

EXAMPLE 3

Experiments were performed during which the effects of two beta-adrenolytic agents propanolol and THPT, on renal function and plasma renin activity (PRA) were studied in sixteen conscious sodium replete dogs. In all experiments renal function was evaluated from effective renal plasma flow (RPF) and glomerular filtration rate (GFR) assessed by measurement of the clearances of para-aminohippuric acid ($C_{PAH}$) and creatinine, respectively. These parameters were measured during two 30 minute control periods, following which, two further measurements were performed over a similar time period, after intravenous administration of either propanolol (0.5 mg/kg n=8), or THPT (0.05

CLINICAL STUDY

EXAMPLE 4

The study was carried out on 20 subjects divided into 4 groups of 5 patients.

Group I

Patients suffering from hypertension and having chronic organic renal insufficiency;

Group II

Patients suffering from hypertension having a normal glomerular filtration rate;

Group III

Normal controls;

Group IV

Patients having chronic organic renal insufficiency but having arterial blood pressure figures which remained normal both when lying down and when standing up.

Each patient received THPT in the form of tablets for 15 days, form $D_1$ to $D_{15}$. One tablet containing 5 mg of THPT hydrochloride was administered each morning at breakfast. The glomerular filtration rate and the renal plasma flow were evaluated using the standard methods of clearance of inulin and para-aminohippuric acid. Plasma renin activity and plasma aldosterone were measured by radio-immunology. These measurements were carried out on day 0 and day fifteen ($D_0$ and $D_{15}$) of the treatment and were subjected to statistical analysis.

Analysis of the results showed (A) Hypertensive patients:
in patients suffering from hypertension and having chronic renal insufficiency (Group I):
a significant average increase in the glomerular filtration rate of 11.70% ($p<0.05$) and
a significant average increase in renal plasma flow of 10.80% ($p<0.01$)

in patients suffering from hypertension without renal insufficiency (Group II):
a significant average increase in the glomerular filtration rate of 29.71% ($p<0.01$)
a significant average increase in the renal plasma flow of 34.78% ($p<0.01$)
(B) Normotensive patients
in normal subjects (Group III):
an average increase in the glomerular filtration rate of 2.95% (statistically not significant=NS) an average increase in the renal plasma flow of 1.94% (N.S.)

in patients having chronic renal insufficiency without hypertension (Group IV):
an average increase in the glomerular filtration rate of 9.15% (N.S.) an average decrease in the renal plasma flow of 7.4% (N.S.)

With regard to plasma renin activity and aldosteronemia, a decrease in the basic values was observed after treatment whichever group was studied. The average decrease for plasma renin activity was 40% when lying down ($p<0.001$) and 58% when standing up ($p<0.001$); for aldosterone it was 37% when lying down (N.S) and 42% when standing up ($p<0.05$).

The systolic and diastolic arterial blood pressure decreases significantly in patients suffering from hypertension. THPT is tolerated well, whether chronic renal insufficiency is present or not, and does not have any side effects so that it is safe for use.

Table 3 summarizes the effects on glomerular filtration rate and renal plasma flow after chronic oral administration of THPT in hypertensive or normotensive subjects with or without renal insufficiency.

TABLE 3

| Group of Patients | Glomerular filtration rate | Renal Plasma flow |
|---|---|---|
| (A) Hypertensive Patients | | |
| with chronic renal insufficiency (Group I) | Increase (11.70%) (S) | Increase (10.80%) (S) |
| without renal insufficiency (Group II) | Increase (29.71%) (S) | Increase (34.78%) (S) |
| (B) Normotensive Patients | | |
| normal subjects (Group III) | Increase (2.95%) N.S. | Increase (1.94%) N.S. |
| with chronic renal insufficiency (Group IV) | Increase (9.15%) N.S. | Decrease (7.4%) N.S. |

S: Statistically significant
N.S.: Statistically not significant

We claim:

1. A method for preventing or treating renal insufficiency, by increasing renal glomerular filtration rate and renal plasma flow, in a hypertensive patient in need thereof, which comprises the step of orally or parenterally administering to said patient a compound selected from the group consisting of 8-(3-tert.-butylamino-2-hydroxypropoxy)-thiachroman, an optical isomer thereof, and an addition salt thereof, in a daily dosage amount of 2 to 10 mg.

2. A method according to claim 1 which comprises administering a 5 mg daily amount of 8-(3-tert.-butylamino-2-hydroxypropoxy)-thiachroman hydrochloride.

3. A method according to claim 1, wherein the 8-(3-tert.-butylamino-2- hydroxypropoxy)-thiachroman, optical isomer thereof, or addition salt thereof is administered in admixture with a pharmaceutically acceptable carrier.

4. A method according to claim 3 in which the carrier is one of those suitable for oral use.

* * * * *